United States Patent [19]

Kamiya et al.

[11] Patent Number: 5,205,745
[45] Date of Patent: Apr. 27, 1993

[54] ARTIFICIAL DENTAL ROOT

[75] Inventors: Takashi Kamiya, Ichihara; Tohru Nonami, Narita; Sachiko Shirakawa, Ichikawa, all of Japan

[73] Assignee: TDK Corporation, Tokyo, Japan

[21] Appl. No.: 684,927

[22] PCT Filed: Aug. 29, 1990

[86] PCT No.: PCT/JP90/01094

§ 371 Date: Jun. 11, 1991

§ 102(e) Date: Jun. 11, 1991

[87] PCT Pub. No.: WO91/03213

PCT Pub. Date: Mar. 21, 1991

[30] Foreign Application Priority Data

Aug. 30, 1989 [JP] Japan ................. 1-223587
Dec. 4, 1989 [JP] Japan ................. 1-314915

[51] Int. Cl.⁵ ........................... A61C 8/00
[52] U.S. Cl. ........................... 433/173; 433/174; 433/201.1
[58] Field of Search ........... 433/173, 174, 175, 176, 433/169, 201.1

[56] References Cited

U.S. PATENT DOCUMENTS

| | | |
|---|---|---|
| 3,590,485 | 7/1971 | Chercheve et al. ............. 433/174 |
| 4,086,701 | 5/1978 | Kawahara et al. |
| 4,185,383 | 1/1980 | Heimke et al. ................. 433/173 |
| 4,229,169 | 10/1980 | Smith et al. .................... 433/174 |
| 4,293,308 | 10/1981 | Hassler et al. ................. 433/173 |
| 4,818,559 | 4/1989 | Hama et al. .................... 433/173 |
| 4,826,434 | 5/1989 | Krueger ........................... 433/174 |
| 5,000,686 | 3/1991 | Lazzara et al. ................. 433/174 |

FOREIGN PATENT DOCUMENTS

| | | |
|---|---|---|
| 2308962 | 9/1973 | Fed. Rep. of Germany ...... 433/173 |
| 4019846 | 1/1991 | Fed. Rep. of Germany ...... 433/173 |
| 48-438 | 1/1973 | Japan . |
| 53-877 | 1/1978 | Japan . |
| 53-2279 | 1/1978 | Japan . |
| 57-75646 | 5/1982 | Japan . |
| 60-85739 | 5/1985 | Japan . |
| 60-135042 | 7/1985 | Japan . |
| 61-142021 | 9/1986 | Japan . |
| 61-191016 | 11/1986 | Japan . |
| 62-172944 | 7/1987 | Japan . |
| 62-133605 | 8/1987 | Japan . |
| 63-174648 | 7/1988 | Japan . |

Primary Examiner—Cary E. O'Connor
Attorney, Agent, or Firm—Oblon, Spivak, McClelland, Maier & Neustadt

[57] ABSTRACT

The present invention relates to an artificial ceramic dental root, wherein the outer circumference portion of the main body of the artificial dental root which has been implanted in the jaw bone is integrally formed of ceramic material; the diameter of a dental neck-corresponding portion of the artificial dental root extending from a part inserted into the top of the jaw bone to at least a part of the dental neck is made larger than that of a base; and a tapered portion is provided between said base and the dental neck-corresponding portion, whereby stress concentration is relieved and the artificial dental root is obtained which is highly resistant to outer forces, especially a force in an oblique direction. Even when a ceramic coated layer is layered over a metallic core to form a layer structure, the ceramic layer is prevented from coming off.

21 Claims, 11 Drawing Sheets

Fig. 5
FIG. 5(A)
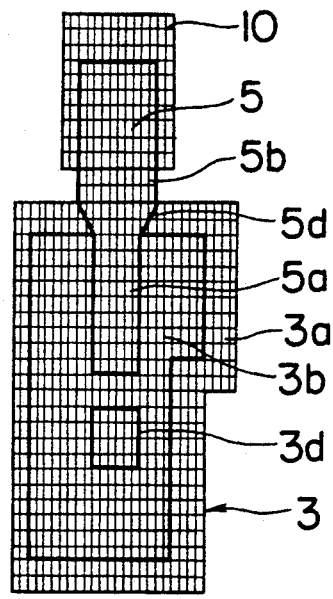
FIG. 5(B)
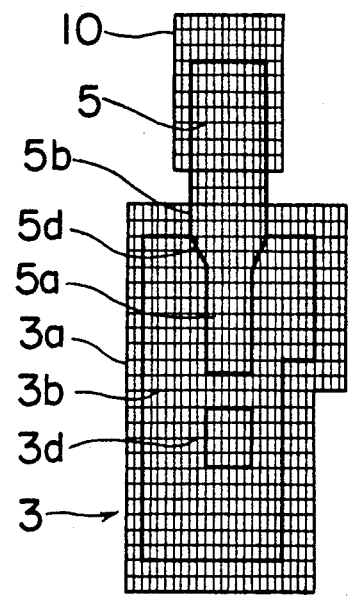
FIG. 5(C)
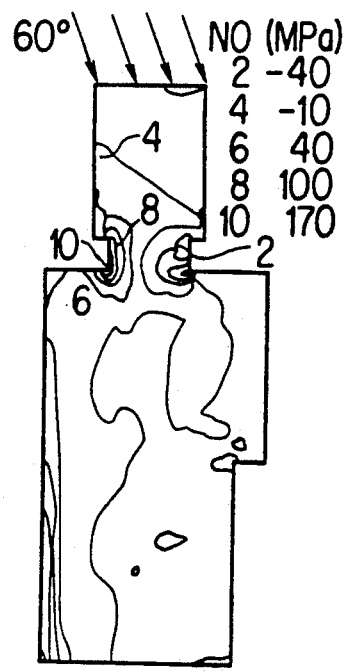
FIG. 5(D)
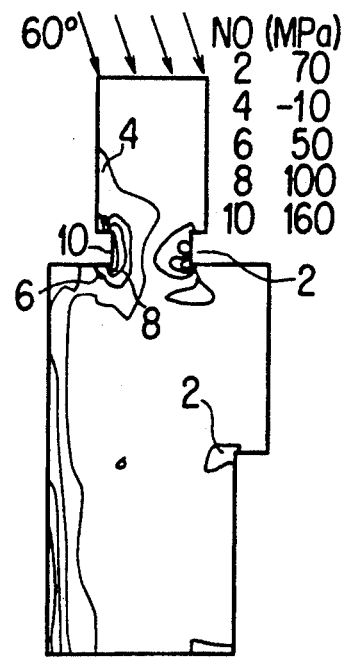

FIG. 7(A)
FIG. 7(B)
FIG. 7(C)
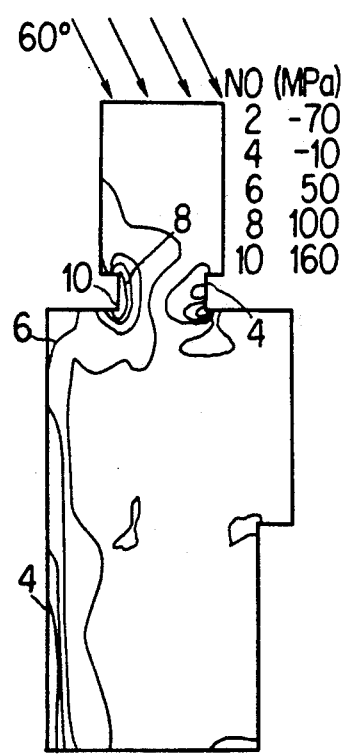
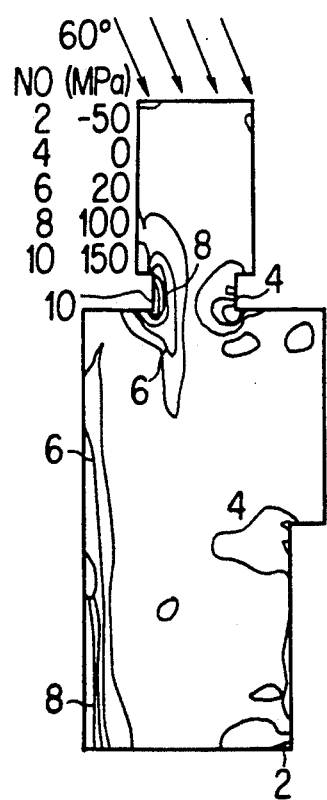
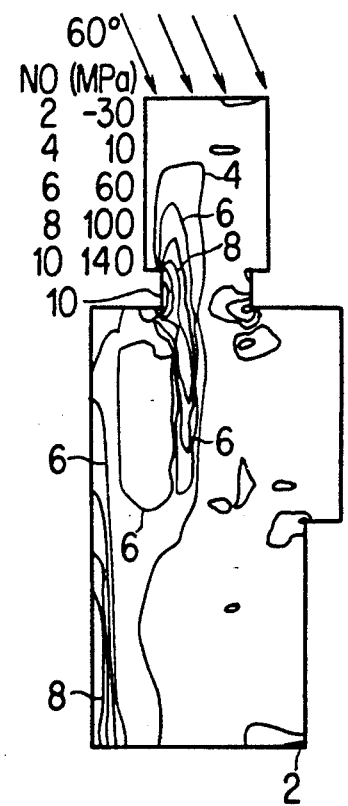

ARTIFICIAL DENTAL ROOT

FIELD OF TECHNOLOGY

The present invention relates to an artificial dental root fixed by implanting it into a hole drilled in the jaw bone, and more particularly to an artificial dental ceramic root.

BACKGROUND TECHNOLOGY

In order to fix an artificial tooth, first, the upper surface of the gingival mucosa is incised; second, a hole is drilled into the jaw bone; third, an artificial dental root is implanted into the hole; fourth, a shock-absorbing material and a crown of the tooth is constructed 2–3 months later, namely, after the artificial dental root has been fixed by newly grown bone.

In such an artificial dental root, generally speaking, threads are cut on one end of a round rod-shaped material so as to prevent the root from coming off, and the other end is used as a crown attaching portion. A hole, whose diameter is almost the same as that of this threaded portion, is drilled in the jaw bone, into which the threaded portion is implanted. The conventional artificial dental root used to be fixed by allowing the new bone to grow between the threads.

Such an artificial dental root, however, requires the drilling in the jaw bone of a hole whose diameter is almost the same as that of the crown-attaching portion. If the diameter of this hole is large, it becomes difficult to drill the hole in the jaw bone in order to implant the artificial dental root into a narrow jaw bone, which leads to frequent injuries to the jaw bone. On the other hand, however, there is a drawback in that if the diameter of the hole, that is, the diameter of the artificial dental root, is made small, the strength required for the root is not obtained, and it is likely to break or become damaged, or at the same time, sink further into the jaw bone owing to a force exerted onto the artificial dental root.

The Japanese Patent Publications Kohkoku Showa 53-2279 and Kohkoku Showa 53-877 and U.S. Pat. No. 4,086,701 (corresponding to the aforementioned two publications) have been known as one which is designed to stabilize and strengthen the artificial dental root with respect to biting impacts.

The aforementioned Japanese Patent Publications 53-2279 provided a horizontal flange member (disk-like flange member) for the artificial dental root which acted as a main stabilizing seat against external force. Although this artificial dental root mainly supported external stress by means of the horizontally extending diske-like flange member, the stress was concentrated onto the thin portion of the disk-like flange member, the portion of which sometimes proved to be insufficient in terms of strength. In particular, though strong against stress applied in a vertical direction, the disk-like flange member was weak against stress exerted in an oblique direction. This indicated that it was practically difficult to provide sufficient strength to relieve the concentration of biting stresses.

Similarly, an artificial dental root equipped with a stopper portion has been disclosed in Japanese Patent Publication Kohkai Showa 60-135042; however, this was not designed to support biting stresses and could not provide sufficient strength and relieve concentrated biting stresses.

In addition, the aforementioned Japanese Patent Publication Kohkoku Showa 53-877 describes an artificial dental root provided with an anchor ring (a washer-like flange member) which is inserted into a cavity in the jaw bone and acts as a stabilizing seat.

Since this washer-like flange member, however, was made of porous ceramics and screwed to the root body, it did not have sufficient strength and stress-relieving action against external stresses even though it was effective in stabilizing the artificial dental root.

In particular, stress was concentrated onto the screw-joint portion, the washer-like flange member was very likely to chip off. It also had a drawback that if a joint portion such as a screw is provided in the implanted part of the bone, this may easily produce a pocket of a nest of baccili.

These drawbacks are particularly noticeable in the case where, in general, mechanically weak calcium phosphate ceramics or bioactive ceramic materials are used in the artificial dental root.

DISCLOSURE OF THE INVENTION

It is one of the objects of the present invention to provide a highly mechanically strong artificial dental root by resolving the above-mentioned drawbacks and relieving external forces during biting, especially the concentration of stresses in an oblique direction.

Another object of the present invention is to provide an artificial dental root which shows little bone destruction or resorption at the contact points between the artificial dental root and the jaw bone.

Yet still another object of the present invention is to provide an artificial dental root which is designed to prevent rotation and/or detachment of ceramics and metallic core in an artificial dental root of ceramics integrated with the metallic core while maintaining the strength at the stress concentrating part.

A further object of the present invention is to provide an artificial dental root having a mechanically strong and simple-to-use implanting tool of an artificial dental bone of ceramics integrated with the metallic core.

The aforementioned objects of the present invention will become apparent from the following description of the invention by way of the preferred embodiments.

That is, the present invention is an artificial dental root characterized in that the circumference of the main body to be implanted into the jaw bone is integrally constructed of ceramic material, that the diameter of a dental neck corresponding portion from the part implanted into the top of the jaw bone to the neck is larger than that of the base of the root, and that the part between the base and the dental neck corresponding portion is tapered.

When part of the artificial dental root is implanted into a hole drilled in the jaw bone, the portion where the maximum stress occurs upon the action of a force onto the artificial dental root 5 is the part which corresponds to the top of the jaw bone 3c comprising dense matter 3a. If this part is made larger than a root base 5a of the artificial dental root in the hole, the stress is relieved, and the strength required for the artificial dental root 5 is obtained. At the same time, the load onto the jaw bone can be lessened because the hole into which the base 5a is implanted can be made smaller. On the other hand, since the parts with larger diameters 5b, 5d are provided upper of the base 5a, the artificial dental root is prevented from sinking into the jaw bone.

In this case, the artificial dental root with a larger diameter is insufficient if it corresponds to the top of the thin jaw bone 3c. Therefore, in order to relieve stresses and obtain strength, it is essential for it to have at least from the portion implanted into the top of the jaw bone 3c to the portion a part of which extends to the dental neck (the portion in the gingiva) (hereinafter referred to as the "dental neck-corresponding portion" 5b of the artificial dental root).

Moreover, since the shoulder between the small-bore base and the large-bore dental neck-corresponding portion is vulnerable to stress concentration and thereby may chip off, it is tapered (R-shaped or in an oblique form, etc.), whereby stress relief is promoted, the sharp shoulder is eliminated, and as a result, the stimulation of the jaw bone and associated bone resorption occur less frequently.

The artificial dental root is integrally constructed together with ceramic material at least in the outer circumferential portion which comes in contact with the jaw bone. Since there is no screwed washer structure in the outer circumferential portion which comes in contact with the bone, and there is little concentration of unnecessary stress, the artificial dental root thus constructed is highly resistant to external force and at the same time rarely produces a pocket of a nest of baccili.

The artificial dental root may be constructed with ceramic material alone. It may also have a metallic core inside and its surface may be covered with a layer of ceramic material.

Because of simplicity of manufacturing and because there is no problem with detachment of the ceramic layer, and in terms of stress distribution (see FIG. 7 described later), it is preferable to construct the artificial dental root with the use of ceramics alone. However, if, as in anterior teeth, a strong stress is exerted in an oblique direction, it is more preferable to use the artificial dental root having a metallic core in order to provide it with a high degree of mechanical strength.

In general, the artificial dental root integrating ceramics and metal are prone to encounter problems such as detachment or breakage of the ceramic layer induced by stress. In the present invention, on the other hand, the portion onto which the maximum stress is exerted is made larger in diameter; therefore, the aforementioned problems such as detachment rarely occur in that the stress is distributed and that the core material is hardly deformed by means of stress.

If the ceramic material is layered over the metallic core, it is essential to prevent them from rotating or detaching as a result of the rotative force of the implanting tool or time-dependent changes (aging) during the period of use. In order to achieve this, it is preferable: to arrange it into an anti-rotative shape using a part of the outer circumference of the metallic core and the ceramic core material connected thereto.

At the same time, it is preferable from a mechanical point of view to furnish the portion that is to be the anti-rotative shape in the interior of the dental neck-corresponding portion having a larger diameter.

The ceramic materials used in accordance with the present invention are the calcium phosphate-derived ceramics such as hydroxyl apatite, tricalcium phosphate, non-calcium phosphate-derived biologically active ceramics which contents CaO and $SiO_2$ as essential components and precipitate calcium phosphates in the body fluid such as diopsite and worastenite, calcium phosphate-derived ceramics which are compounded and strengthened by means of whisker made by diopsite or anosite, etc., bioglass and alumina. Biologic ceramics should preferably be those having biological activity in terms of bioaffinity; however, these materials lack strength in general. For this reason, if constructed in such a way that its strength can be improved on as in the present invention, an artificial dental root is obtained which is excellent in both bioaffinity and strength.

Among ceramics, it is most preferable to use non-calcium phosphate-derived biologicall active ceramics which contains CaO and $SiO_2$ as essential components such as diopsite and worastenite, or calcium phosphate-derived ceramics which are compounded and strengthened by means of a whisker made by diopside or anosite, etc., because these materials are biologically active and very strong.

The artificial dental root according to the present invention is applied for two types; that is, a one-piece type in which the portion implanted into the jaw bone (the main body) is integrated with the crown attaching portion (the upper structure), and a two-piece type in which both bodies are separable. The two-piece type is more preferable in that the root body is first implanted to be stabilized such that no external force is exerted thereonto, and the upper structure can be jointed after the fixation of the dental root.

BRIEF DESCRIPTION OF THE DRAWINGS

FIGS. 5(A) and 5(B) are model diagrams of the implantation structure shown in FIGS. 4 and 1.

FIGS. 5(C) and 5(D) are stress-distribution diagrams of the models shown in FIGS. 5(A) and 5(B).

FIG. 7 is a stress-distribution diagram of various materials.

OPTIMAL EMBODIMENTS OF THE INVENTION

Figure 1:
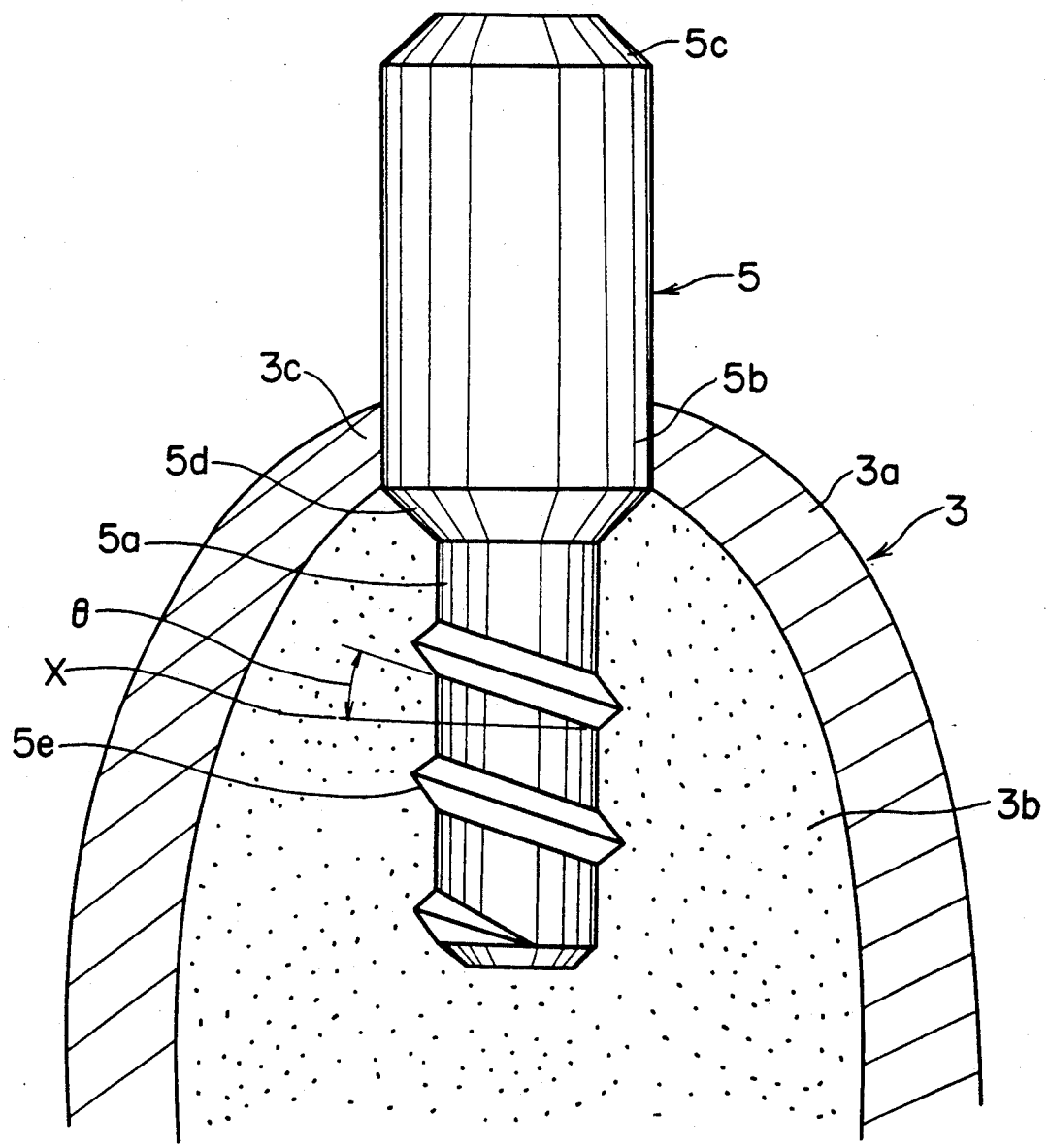
FIG. 1 is a side view of an embodiment showing the artificial dental root fixed to the jaw bone according to the present invention.

FIG. 1 is a side view showing an embodiment of the one-piece type of artificial dental root fixed to the jaw bone according to the present invention. In the artificial dental root 5 in this embodiment, the diameter of the dental neck-corresponding portion 5b which corresponds to the top 3c of the jaw bone 3 to the top (the crown attaching portion) 5c of the artificial dental root is made larger with respect to the base 5a of the artificial dental root implanted into the jaw bone 3. The bottom 5d of the dental neck-corresponding portion 5b is tapered in order to relieve biting stresses. Numeral 5e is a helically formed thread around the base 5a in order to prevent the implant element from coming off and rotating.

The oblique angle $\theta$ of the helically formed thread with respect to line X which is at a right angle to the axis of the artificial dental root is preferably from 8 to 25 degrees; more preferably, it is from 10 to 20 degrees. The reason for this is that since the tissue that the helically formed thread comes into contact with is a spongy tissue 3b and if the oblique angle is smaller than the aforementioned, and the number of windings is larger, the amount of the bone forming between the threads becomes small and thereby the support strength declines. This also cause easier destruction of the jaw bone which comes into contact with the threads. On the other hand, this is because the implanting procedure becomes difficult if the oblique angle exceeds the aforementioned range. In order to enhance the effect of the screwing effect on the spongy tissue 3b, it is preferable that the crest of the thread is from 0.2 to 1.0 mm high, and its pitch is 1.0 mm or longer.

Figure 2:
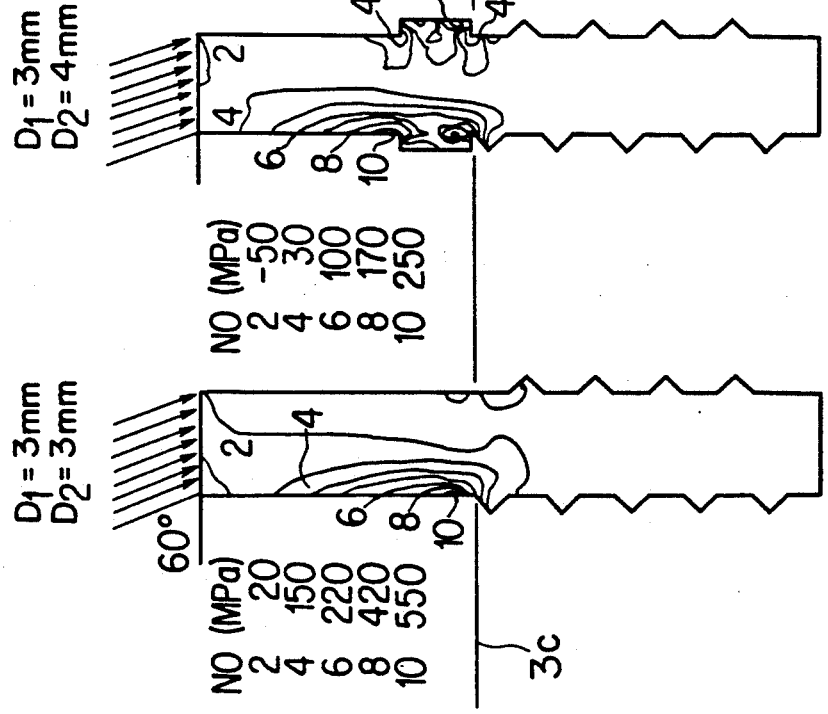
FIG. 2 is a stress-distribution diagram prepared by computer simulation of the diameters corresponding to various dental neck corresponding portion.

FIG. 2 is a diagram showing results of the stress distribution obtained by computer simulation using an artificial dental root that has as the material hydroxyl apatite reinforced by mixing in ceramic whisker on the assumption that a force of 60 kg is exerted at an angle of 60 degrees to the artificial dental root in order to determine how the stress distribution changes by altering the diameter of the dental neck-corresponding portion 5b with respect to the base 5a. Each stress distribution is an example in which the diameter of the dental neck-corresponding portion D2 (See FIG. 3) is altered to 3 mm (A), 4 mm ((B)–(D)) and 5 mm (E) and the length of the dental neck-corresponding portion 5b is altered ((B)–(D)) in the case where the diameter D1 of the base 5a (see FIG. 3) is 3 mm. The line 3c in FIG. 2 represents the top of the jaw bone.

As can be seen from FIGS. 2(A)–2(E), the portion where the maximum stress occurs is one which corresponds to the top 3c of the jaw bone; the main stress concentrates on the dental neck-corresponding portion 5b from the top of the jaw bone to at least a part of the dental neck.

Conversely, the stress onto the base 5a which corresponds to the interior of the jaw bone is small.

On the other hand, as is clear from the comparison of FIG. 2(A) and FIGS. 2(B)–2(D), the maximum stress is reduced by approximately a half or more by increasing the diameter of the dental neck-corresponding portion 5b from 3 mm to 4 mm. Furthermore, as can be seen from the comparison of FIGS. 2(B)–2(D) and 2(E), the maximum stress is reduced to approximately a half by increasing the diameter D2 of the dental neck corresponding portion 5b from 4 mm to 5 mm.

In this way, increasing the diameter D2 of the dental neck-corresponding portion 5b is extremely effective in reducing the stress exerted. At the same time, as is clear from the comparison of FIGS. 2(B) and 2(C)–2(D), it is sufficient to give only the dental neck-corresponding portion 5b a large diameter. Even though the top 5c is rendered large in diameter, the stress is not relieved.

In FIGS. 2(C)–2(E) where each implant element is tapered, the maximum stress is exerted onto the flat portion of the large diameter, whereas in FIG. 2(B) in which the implant element is not tapered, the stress concentrates on the shoulder. For ceramic materials. it is preferable to avoid the concentration of stress because of lack of strength. Moreover, it is more preferable to taper the shoulder (R-shaped or inclined surface etc.) in order to relieve the stimulation to the jaw bone.

Figure 3:
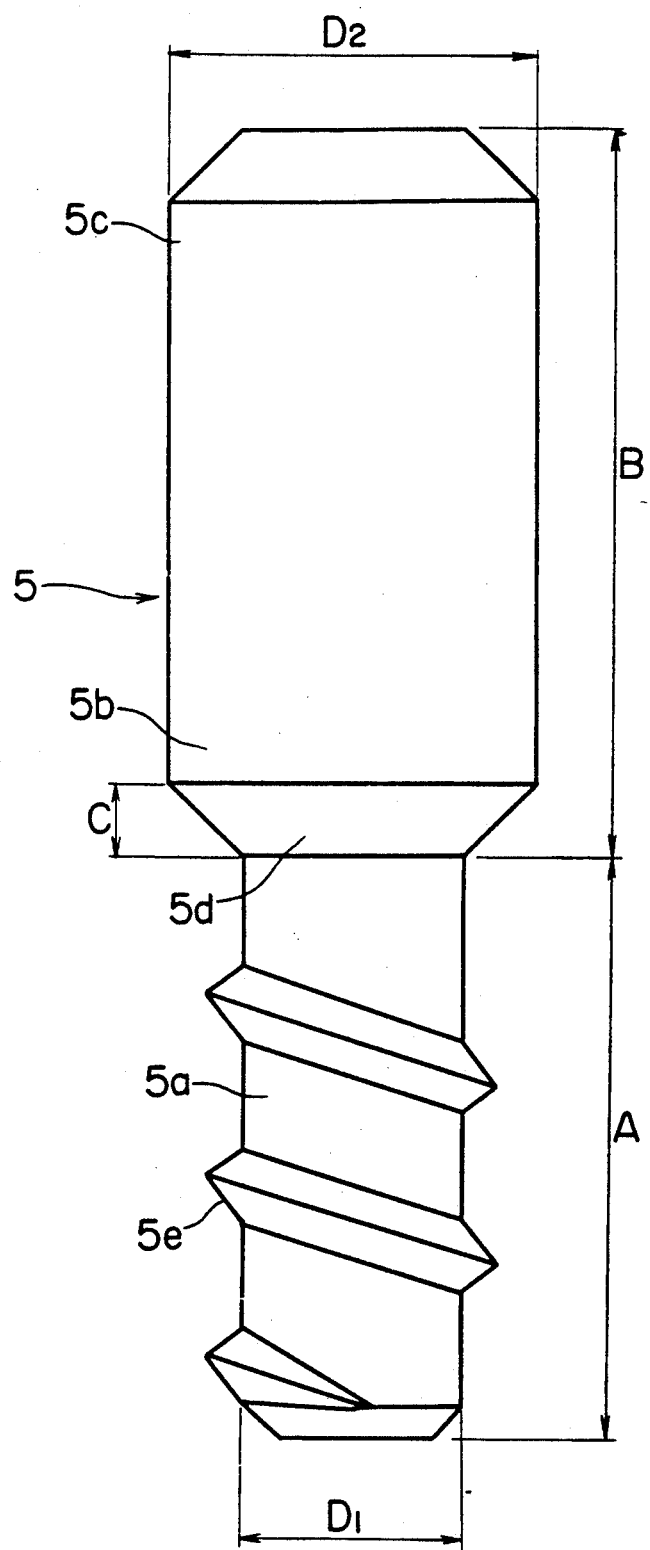
FIG. 3 illustrates the dimensions of this embodiment.

FIG. 3 represents each dimension of the artificial dental root illustrated in FIG. 1, showing a one-piece type.

The diameter D1 of the base 5a is 2 mm–8 mm, preferably 3 mm–5 mm. If the diameter D1 of the base 5a is smaller than 2 mm, the required strength can hardly be obtained, and if it is larger than 8 mm, it is inconvenient in that the hole drilled into the jaw bone becomes larger than necessary. At the same time, the diameter D2 of the dental neck-corresponding portion 5b is 3 mm–14 mm, preferably 5 mm–10 mm. If the diameter D2 of the dental neck-corresponding portion 5b is smaller than 3 mm, required strength can hardly be obtained, and if it is larger than 14 mm, it is convenient in that the hole drilled in the jaw bone becomes extremely large, which leads to a decrease in the strength of the top of the jaw bone.

In addition, the ratio of the diameter D1 of the base 5a to the diameter D2 of the dental neck-corresponding portion 5b, namely, D1/D2 is 0.15–0.80, preferably 0.3–0.7. If the ratio D1/D2 is smaller than 0.15, the diameter of the base 5a cannot be secured, and if it is larger than 0.80, the purpose to maintain the hole 7 small and the strength high cannot be achieved.

At the same time, the length of the dental neck-corresponding portion 5b should preferably cover at least the top 3a of the jaw bone and the dental neck, that is at least 1 mm or more although it depends on the site of the jaw bone. In the case of a two-piece type, the length should preferably be 2 mm–4 mm, while in the case of a one-piece type, the length B of the dental neck-corresponding portion 5b to the top (the crown attaching poryion) 5c is usually 5 mm–16 mm, preferably 7 mm–11 mm.

In addition, the ratio of the protruded amount in an outward direction (E=(D2−D1)/2) of the dental neck-corresponding portion 5b to the length B from the dental neck-corresponding portion 5b to the top 5c, namely E/B, should preferably be 1.5 or less in order to prevent stress concentration and secure strength. In the case of the one-piece type, it is preferably 0.02–0.2, while in the case of the two-piece type, it is preferably 0.2–1.0.

The length A of the base 5a is selected depending on the conditions of the tooth and jaw bone used; when taking into account the distance between the top of the jaw bone 3 and the jaw duct through which the nerves pass, it is 2 mm–18 mm, preferably 6 mm–11 mm.

At the same time, the ratio of the length of the base 5a to the length from the dental neck-corresponding portion 5b to the top 5c, namely A/B, should more preferably range between 0.15–7.0. In the case of the one-piece type it is preferably 1–2, while in the case of the two-piece type, it is preferably 3-6. Moreover, the length of the tapered portion 5d is 0.5 mm-5 mm, preferably 1 mm-2 mm.

Figure 4:
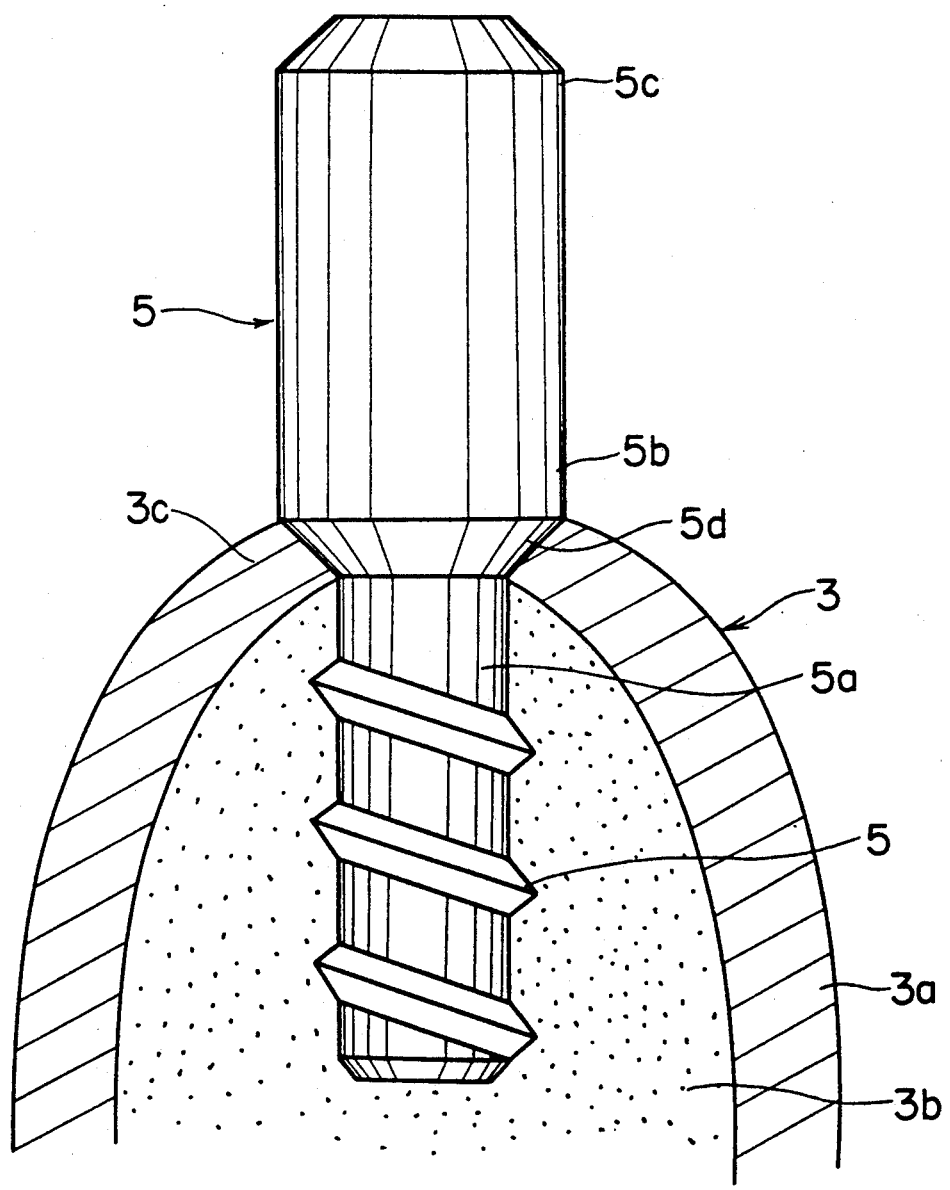
FIG. 4 is a sectional view of another implantation case of the artificial dental root in FIG. 1.

FIG. 4 is an embodiment wherein the artificial dental root is attached by disposing in the top 3c of the jaw bone 3 the tapered portion 5d which has been formed in the bottom of the dental neck-corresponding portion 5b. From such an arrangement is obtained the stress relieving effect close to that of the embodiment in FIG. 1.

FIGS. 5(A) and 5(B) are models including the jaw bone 3 and the crown 10 of the embodiments in FIGS. 4 and 1, respectively (3d represents the jaw duct). FIGS. 5(C) and 5(D) are stress distribution diagrams showing results obtained by computer simulation of stress distribution wherein a load of 60 kg is applied at an oblique angle of 60 degrees in the models of FIGS. 5(A) and 5(B), respectively, As can be seen from FIG. 5, even though the tapered portion 5d is fixed by disposing it to the top 3c of the jaw bone 3, the maximum stress increases only 10 MPa from 160 MPa to 170 MPa as compared with the embodiment of FIG. 1. This indicates that the structure where the tapered portion 5d is fixed to the top 3c of the jaw bone is effective.

Figure 6:
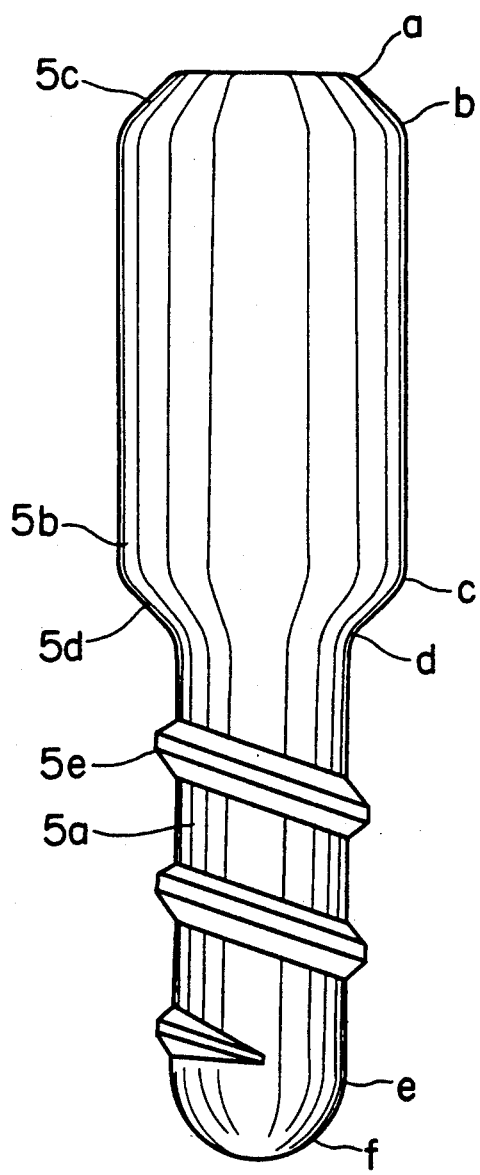
FIG. 6 is a side view showing another embodiment of the artificial dental root according to the present invention.

FIG. 6 is another embodiment of the present invention, wherein the angular portions a-e have been formed into an R surface. The tip 5e of the helical thread is formed into a smooth or R surface, and the lower end f of the base 5a is shaped into a sphere. If the structure is shaped like this, stress concentration to the angular portions is relieved, ceramic material is prevented from chipping off, and a artificial dental root having higher strength is obtained. In addition, the stimulation of the angular portions to the jaw bone is relieved, which in turn helps prevent the occurrence of bone resorption caused by such stimulation.

Fig. 7 shows the stress distribution calculated by changing materials in a model as in FIG. 5 based on the structure of FIG. 1, wherein (A) indicates the artificial dental root of hydroxyl apatite (HAP) reinforced with diopsite whisker, (B) the artificial dental root made of titanium alone, and (C) the artificial dental root of alumina alone. In the present invention, it is of course possible to use, as material for the artificial dental root, titanium or alumina.

As can been seen from FIG. 7, however, in the case of the HAP reinforced with diopsite whisker, the stress of the part under the dental neck corresponding portion 5b becomes very small owing to the rate of elasticity. In the case of titanium and alumina, on the other hand, stress occurs even in the bottom of the artificial dental root. In the present invention, therefore, wherein the strength of the dental neck-corresponding portion 5b is increased, this structure may be preferable in that the use of the HAP which has been reinforced with whisker of diopsite, etc. suits stress distribution and applies the stress to the highly strong dense tissue 3a rather than the less strong spongy tissue 3b.

FIG. 8 shows another embodiment of the two-piece type artificial dental root according to the present invention, wherein (A) indicates a plane view, (B) a vertical sectional view, and (C) and (D) are the sectional views taken along lines E—E and F—F of (B), respectively. Numeral 5 represents the main body of the artificial dental root of ceramic material (hereinafter referred to as the main body), 2 shows the metallic core material of said main body and 6 indicates the upper structure.

Figure 8A:
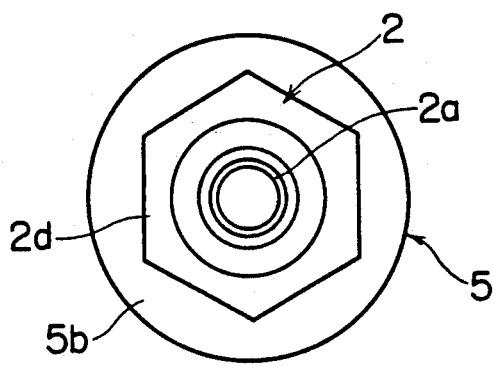
FIG. 8(A) is a plane view of the other embodiment of the artificial dental root according to the present invention.
Figure 8B:
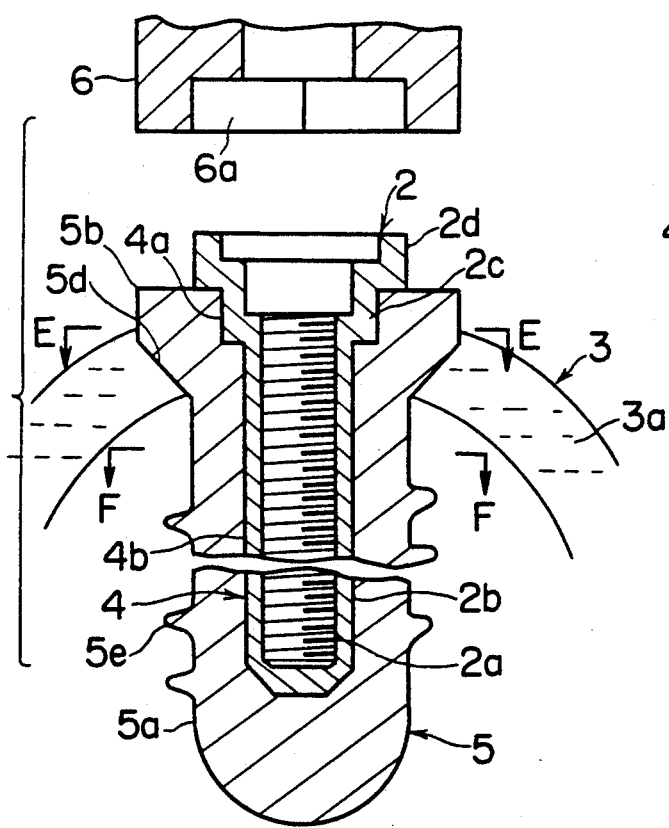
FIG. 8(B) is a vertical sectional view of FIG. 8(A).
Figure 8C:
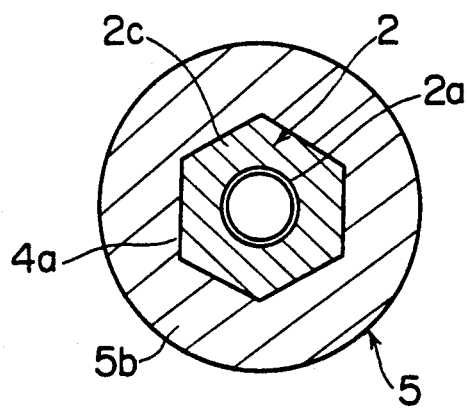
FIGS. 8(C) and 8(D) are sectional views taken along the line E—E and line F—F of FIG 8(B), respectively.
Figure 8D:
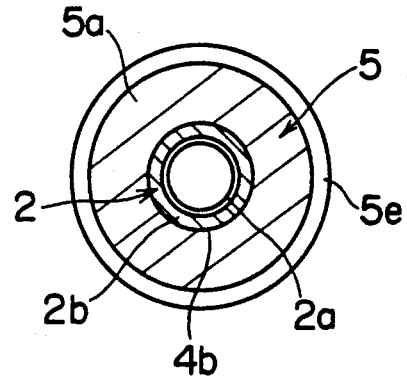

In FIG. 8(B), as described above, the diameter of the dental neck-corresponding portion 5b is made larger than that of the base 5a, and the portion between them is the tapered portion 5d.

In this structure, stress concentration is relieved in the layered structure with the metallic core, whereby the ceramic portion is prevented from coming off or chipping off.

The main body 5 is constructed of the aforementioned ceramic material, in the center of which a core-attaching hole 4 is disposed.

Said core-attaching hole 4 comprises a portion 4a which is provided top of the hole and whose section is an anti-rotative shape such as a polygon or an ellipse (a hexagon in this example): and a portion 4b which is provided from the bottom of the hole 4 and whose section is circular.

The core 2, on the other hand, is constructed of titanium, titanium alloy, stainless-steel, etc., the interior of which is a cylinder having a screw hole 2a for screwing the upper structure 6. The outer circumference of said core 2 is protruded upward and comprises a circular insertion 2b which is inserted into the main body 5; the first anti-rotative shaped portion 2c (a hexagon in this example) which is inserted into the anti-rotative shaped hole 4a; and the second anti-rotative shaped portion 2d (a hexagon in this example) which protrudes upward from the main body 1 and is larger than the first anti-rotative shaped portion 2c.

The upper structure 6 is combined with the top of the main body 5 and has an anti-rotative shaped hole 6a which is inserted into the second anti-rotative shaped portion 2d of the above-mentioned core 2.

In this artificial dental root, into the circular hole 4b and the anti-rotative shaped hole 4a of the ceramic main body 5 are inserted the circular portion 2b of the core 2 and the first anti-rotative shaped portion 2c, respectively. By so doing, the core 2 is fixed to the main body 5.

In the upper structure 6, the second anti-rotative shaped portion 2d which protrudes from the upper surface of the main body 5 is inserted into the anti-rotative shaped hole 6a of the upper structure 6 and connected to the main body 5 using a screw (not shown) which is screwed into the screw hole 2a of the core 2.

In the above-mentioned structure, the core 2 is prevented from rotating with respect to the main body 5 by insertion of the first anti-rotative shaped portion 2c in the outer circumference of the core 2 into the anti-rotative shaped hole 4a of the main body 5. At the same time, the upper structure 6 is prevented from rotating by insertion of the anti-rotative shaped portion 2d in the outer circumference of the upper protruding portion of the core 2 into the anti-rotative shaped hole 6a of the upper structure 6.

In addition, if the shape of the second anti-rotative shaped portion 2d is so formed as to be inserted into the implanting tool of the artificial dental root, this anti-rotative shaped portion 2d per se may be used as the inserting portion into the implanting tool. In particular, as described above, the main body 5 of the artificial dental root and the metallic core 2 are prevented from rotating by means of the first anti-rotative shaped portion 2c. Because of this, there is no possibility that the ceramic layer will chip off rotate, and they may be used as the simple and strong inserting portion of the implanting tool.

In addition, the sites where the anti-rotative shaped portion 2c of the metallic core 2 and the anti-rotative shaped hole 4a of the artificial dental root body are formed should include at least the interior of the dental neck-corresponding portion 5b which has been formed into the aforementioned large diameter in order to secure sufficient strength. This is designed to alleviate stress concentration even though a powerful rotative force is exerted.

Incidentally, for both anti-rotative shaped portions (2c and 2d) and both anti-rotative shaped holes (4a and 6a), polygonal shapes such as a tetragons, hexagons and ellipses, etc. may be used. For ease of use, a hexagon is preferable.

The methods to layer ceramics over the metallic core include ultra-plastic bonding, heat-press molding, and heat-static pressure press molding.

Figure 9A:
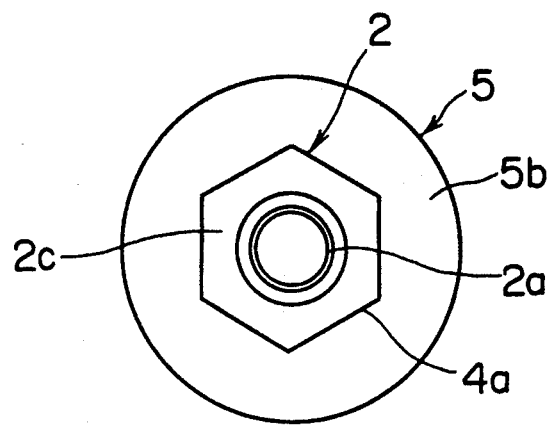
FIG. 9(A) is a plane view showing the other embodiment of the artificial dental root according to the present invention.
Figure 9B:
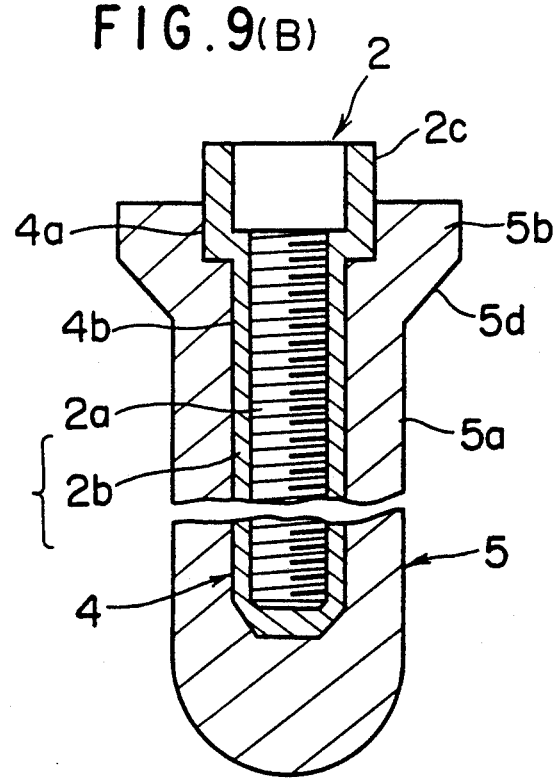
FIG. 9(B) is a vertical sectional view of FIG. 9(A).

FIG. 9(A) is a plane view showing another embodiment of the present invention. FIG. 9(B) is a vertical sectional view of FIG. 9(A). The embodiment differs from the embodiment of FIG. 8 only in the upper shape of the core 2; the upper part of the core 2 is formed in such a way that it protrudes by extending the inserting portion 2c which is inserted into the anti-rotative shaped hole 4a. In this embodiment, the process of the core 2 is facilitated more easily than the core of FIG. 8. In order to stabilize the connection with the implanting tool and prevent the upper structure 6 from rotating, it is more effective to render the polygonal portion 2d larger as shown in FIG. 8 to prevent rotation.

Figure 10A:
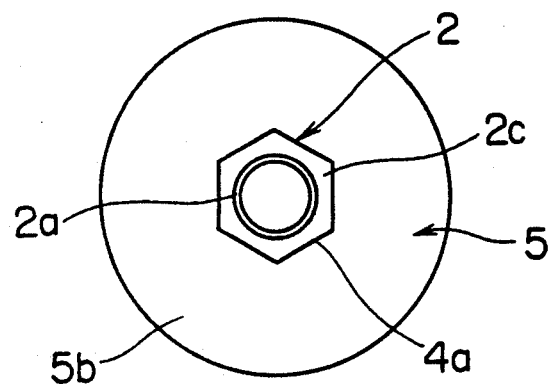
FIG. 10(A) is a plan view showing the other embodiment of the artificial dental root according to the present invention.
Figure 10B:
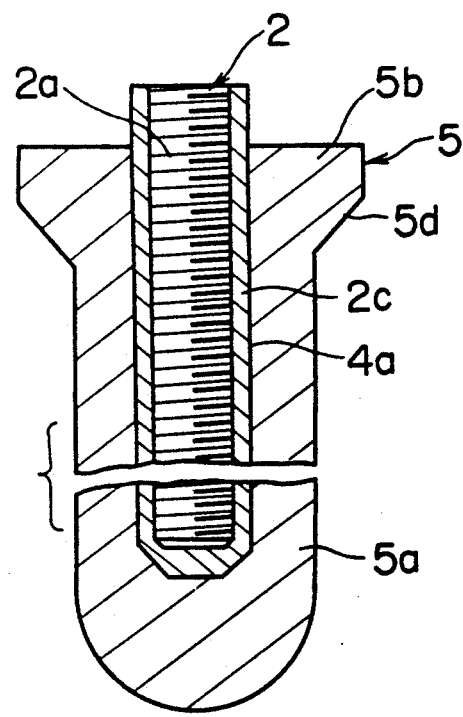
FIG. 10(B) is a vertical sectional view of FIG. 10(A).
Figure 11:
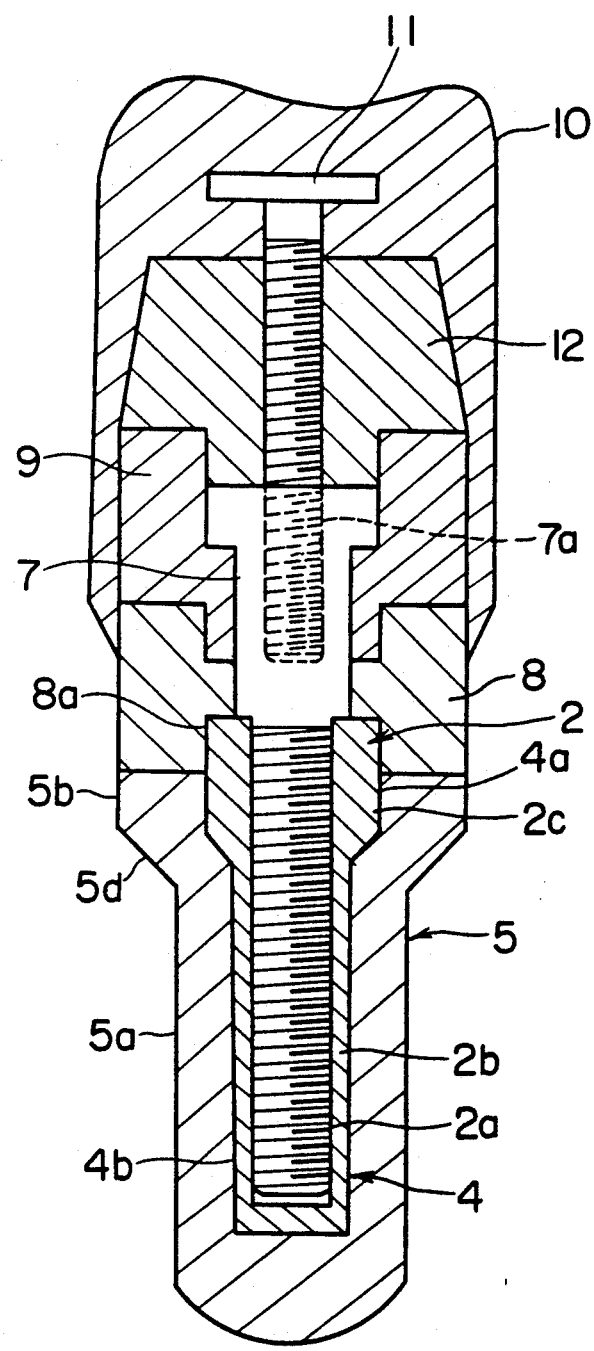
FIG. 11 is a vertical sectional view showing an embodiment of the artificial tooth which is constructed of the artificial dental root according to the present invention.

FIG. 10 is another embodiment of the present invention. The attaching hole of the main body 5 is formed into an anti-rotative shaped hole 4a over its entire length, and at the same time, the core 2 is also made, in the outer circumference, into an anti-rotative shaped portion 2c over its entire length. This embodiment is advantageous in that the core 2 is easily processed. FIG. 11 is a vertical sectional view showing an embodiment of the artificial dental root constructed according to the present invention. A dental neck ring 8 (numeral 8a is a polygonal hole into which the polygonal shaped portion 2c in the outer circumference of the core material 2 is inserted) and the intra-crown lower ring 9 are fixed to the core 2 and the main body 1 by means of the dental root screw 7 which is screwed into the screw hole 2a of the above-mentioned core 2. Into the screw hole 7a which is furnished in the center and from the upper part of the dental root screw is screwed the crown screw 11 which is integrally molded with the crown 10 through the inner crown 12, whereby the artificial dental root is constructed. Incidentally, the dental root screw 7 and the crown screw 11 are made of titanium; the dental neck ring 8 is made of ceramics or titanium; the intra-crown lower ring 9 is made of titanium; the crown 10 is made of porcelain, platinized gold or polymers; and the inner crown 12 is made of titanium, platinized gold or polymers. Needless to say, the artificial tooth constructed in accordance with the present invention is not restricted to this embodiment.

In order to embody the present invention, an adhesive agent, etc. may be supplementally applied to the inserting portion so that the binding strength of the inserting portion can be enhanced.

Advantages of the Invention

In accordance with the present invention, since the diameter of the dental neck-corresponding portion 5b which is inserted into the top 3c of the jaw bone is made larger than the diameter of the base 5a, and since the tapered portion 5d is furnished between a large-bore dental neck-corresponding portion 5b and the small-bore base 5a, stress is relieved at the portion where the maximum stress occurs, and it is possible to provide the artificial dental root with greater strength, especially with respect to the stress in an oblique direction.

At the same time, since the diameter of the base 5a becomes relatively small, the likelihood that the jaw bone will be damaged is alleviated, and it is easy to implant the artificial dental root in a small jaw bone.

Furthermore, even though the sectional area of the artificial dental root 5 is small in the interior of the jaw bone, the sectional area of the artificial dental root disposed at the top of the 5c is large; for this reason, the artificial dental root is prevented from sinking down owing to a force applied to it vertically.

In addition, since the outer circumference of the artificial dental root body is integrally formed with ceramic material, there is little concentration of unnecessary stress, and there are also few pockets for a nest of bacilli to develop.

At the same time, even if the ceramic material is layered over metallic core 2, there are few problems with the implant element coming off because the portion where stress is concentrated is formed into a large diameter in order to relieve it.

Furthermore, if, at least, the metallic core which is in the interior and central part of the large-bore dental neck-corresponding portion 5b is formed into an anti-rotative shape, sufficient rotation prevention is obtained while maintaining strength.

Furthermore, a part of the anti-rotative structure is applied to the inserting portion of the implanting tool of the artificial dental root, which permits an easy and stable implanting procedure.

Furthermore, if the helical thread 5e is formed in a specific range, sufficient fixation is achieved while preventing the destruction of the spongy tissue.

Furthermore, if the angular part of the artificial dental root is formed into a rounded surface, the stimulation to the jaw bone is reduced and bone resorption is prevented from occurring while keeping ceramic material from chipping off owing to stress.

We claim:

1. An artificial dental root comprising a main body to be implanted into the jaw bone and an upper structure to be attached with a crown;

wherein the main body and the upper structure are separable, and the circumference of the main body is integrally constructed of ceramic material, the main body comprising a large diameter dental neck corresponding portion to be implanted into dense matter of the top of the jaw bone and a smaller diameter base of the root, and the part between the base and the dental neck corresponding portion is tapered, wherein said neck corresponding portion has a diameter of 3–14 mm and said base has a diameter of 2–8 mm, and wherein a ratio of the base diameter divided by the neck corresponding portion diameter is in the range of 0.15–0.8.

2. The artificial dental root as defined in claim 1 wherein the main body of the artificial dental root has a metallic core in the center.

3. The artificial dental root of claim 1, wherein the base has a diameter of 3–5 mm and the neck corresponding portion has a diameter of 5–10 mm, and wherein the ratio of base diameter to neck corresponding portion diameter is in the range of 0.3–0.7.

4. The artificial dental root of claim 3, wherein said part which is tapered has an axial length of 0.5–5 mm.

5. The artificial dental root of claim 3, wherein said base has a length of 2–18 mm.

6. The artificial dental root of claim 3, wherein said part which is tapered has an axial length of 0.5–2 mm.

7. The artificial dental root of claim 3, wherein said base has a length of 6–18 mm.

8. The artificial dental rot of claim 1, wherein the root is formed of a material having a rate of elasticity such that upon application of an oblique force, stresses in the root below the neck corresponding portion are reduced.

9. The artificial dental root of claim 8, wherein said material includes hydroxyl apatite reinforced with ceramics whisker.

10. The artificial dental root of claim 9, wherein said whisker is diopsite whisker.

11. The artificial dental root of claim 8, wherein said material comprises non-calcium phosphate-derived biologically active ceramics containing CaO and $SiO_2$ as essential components and precipitate calcium phosphates in a body fluid.

12. The artificial dental root of claim 11, wherein said material comprises one of diopsite and worstenite.

13. An artificial dental root comprising a main body to be implanted into the jaw bone and an upper structure to be attached with a crown;
wherein the main body and the upper structure are separable, and the circumference of the main body is integrally constructed of ceramic material,
the main body comprising a larger diameter dental neck corresponding portion to be implanted into dense matter of the top of the jaw bone and a smaller diameter base of the root,
and the part between the base and the dental neck corresponding portion is tapered;
wherein the main body of the artificial dental root has a metallic core in the center;
wherein a core attaching hole of an anti-rotative shape is provided in a portion including an interior and central portion of the dental neck-corresponding portion;
an anti-rotative shaped portion which is formed in at least a part of the outer circumference of the metallic core is inserted into the anti-rotative shaped hole in order to prevent it from rotating;
an upper end of the metallic core protrudes from the upper surface of the main body of the dental root;
and the outer circumference of the protruded portion is formed into an anti-rotative shape and is inserted into an anti-rotative shaped hole of the upper structure.

14. The artificial dental root as defined in claim 13, wherein the anti-rotative shaped portion is polygonal; and the upper end of said metallic core serves as an inserting portion for an implanting tool.

15. The artificial dental root as defined in claims 13 or 14, wherein a helical thread is formed around said base said helical thread extending at an oblique angle with respect to a direction orthogonal to an axis of the artificial dental root, and wherein said oblique angle is set at 8 degrees to 25 degrees.

16. The artificial dental root as defined claims 1, 13 or 8 wherein angular parts of the artificial dental root are formed into rounded surfaces.

17. An artificial dental root comprising a main body to be implanted into the jaw bone and an upper structure to be attached with a crown;
wherein the main body and the upper structure are separable, and the circumference of the main body is integrally constructed of ceramic material,
the main body comprising a larger diameter dental neck corresponding portion to be implanted into dense matter of the top of the jaw bone and a smaller diameter base of the root,
and the part between the base and the dental neck corresponding portion is tapered,
said artificial dental root formed of a material having an elasticity such that when said root is implanted, stresses resulting from application of an oblique force are concentrated in the neck corresponding portion at least a portion of which is implanted into the highly strong dense tissue of a jaw.

18. The artificial dental root of claim 17, wherein said material includes hydroxyl apatite reinforced with ceramics whisker.

19. The artificial dental root of claim 18, wherein said whisker is diopsite whisker.

20. The artificial dental root of claim 17, wherein said material comprises non-calcium based phosphate-derived biologically active ceramics which contain CaO and $SiO_2$ as essential components and precipitate calcium phosphates in a body fluid.

21. The artificial dental root of claim 20, wherein said material comprises one of diopsite and worstenite.

* * * * *